United States Patent

Chun et al.

[11] Patent Number: 6,124,122
[45] Date of Patent: Sep. 26, 2000

[54] PROCESS FOR PREPARING OPTICALLY PURE (S)-3-HYDROXY-γ-BUTYROLACTONE

[75] Inventors: Jongpil Chun; Yik-haeng Cho; Young Mi Park; Kyoung Rok Roh; Hosung Yu; Dae Il Hwang, all of Daejeon, Rep. of Korea

[73] Assignee: Samsung Fine Chemicals Co., Ltd., Rep. of Korea

[21] Appl. No.: 09/359,678

[22] Filed: Jul. 23, 1999

[30] Foreign Application Priority Data

Jul. 24, 1998 [KR] Rep. of Korea .................. 98-29912

[51] Int. Cl.[7] .................. C12P 17/04; C07D 307/33
[52] U.S. Cl. .................. 435/126; 549/313; 435/74
[58] Field of Search .................. 549/313; 435/74, 435/126

[56] References Cited

U.S. PATENT DOCUMENTS

| | | | |
|---|---|---|---|
| 3,791,865 | 2/1974 | Hurst et al. | 127/32 |
| 3,922,200 | 11/1975 | Guillaume et al. | 195/31 |
| 3,986,890 | 10/1976 | Richter et al. | 127/38 |
| 4,138,484 | 2/1979 | Fuxe | 424/247 |
| 4,447,532 | 5/1984 | Coker et al. | 435/99 |
| 4,612,284 | 9/1986 | Pickens et al. | 435/96 |
| 4,855,232 | 8/1989 | Takasaki | 435/97 |
| 5,292,939 | 3/1994 | Hollingsworth | 562/515 |
| 5,319,110 | 6/1994 | Hollingsworth | 549/313 |
| 5,374,773 | 12/1994 | Hollingsworth | 562/587 |
| 5,506,353 | 4/1996 | Subramaniam | 536/103 |
| 5,808,107 | 9/1998 | Hollingsworth | 549/323 |

FOREIGN PATENT DOCUMENTS

| | | |
|---|---|---|
| 451143 A2 | of 1989 | European Pat. Off. . |
| 64-13069 | of 1989 | Japan . |
| 4-149151 | of 1992 | Japan . |
| 4-158795 | of 1992 | Japan . |
| 6-172256 | of 1994 | Japan . |
| WO 93/06826 | 4/1993 | WIPO . |
| WO 94/05639 | 3/1994 | WIPO . |
| WO 98/04543 | 5/1998 | WIPO . |
| WO99/05092 | 4/1999 | WIPO . |

OTHER PUBLICATIONS

J. Am. Chem. Soc., 105, 5925–5926 (1983).
J. Am. Chem. Soc., 117, 1181 (1995).
J. Am. Chem. Society, 2245–2247 (1953).
J. Chem. Soc., 1924–1931 (1960).
J. Chem. Soc., 1932–1938 (1960).
J. Am. Chem. Soc., 1431–1435 (1955).
J. Am. Chem. Soc., 81, 3136 (1959).
Bull. Chem. Soc. Jpn., 61, 2025 1988.
J. Org. Chem., 50, 1144 (1985).
Tetrahedron Letter, 46, 4277 (1990).
Tetrahedron Letter, 33, 2279 (1992).
Tetrahedron Lett., 507 (1992).
Tetrahedron Lett., 31, 267–270 (1990).
Chem. Lett., 1389–1392 (1984).
J. Res. Natl. Bur. Standards., vol. 32, No. 2, p. 45 (1944).
Can. J. Chem., 65, 195 (1987).
Carbohyd. Res., 11, 17–25 (1969).
Starch 41 Nr. 8, S. 303–309 (1989).
Synthesis, 597–613 (1997).
J. Chromatography, 549, 113–125 (1991).
Methods Carbohydr. Chem., 10, 231–239 (1994).
Methods Carbohydr. Chem., 10, 245–248 (1994).
Encyclopedia of Chemical Technology, vol. 21, p. 495.

*Primary Examiner*—Bernard Dentz
*Attorney, Agent, or Firm*—Finnegan, Henderson, Farabow, Garrett & Dunner LLP

[57] ABSTRACT

The present invention relates to a process for preparing optically pure (S)-3-hydroxy-γ-butyrolactone expressed by the following Formula 1 and more particularly, to a process that enables preparing optically pure (S)-3-hydroxy-γ-butyrolactone economically in large quantities, by:

(a) Preparing α-(1,4) linked oligosaccharide with adequate sugar distribution by reacting amylopectin which is easily available from natural product with enzyme under a specific condition; and (b) Performing oxidation, esterification and cyclization sequentially under a specific condition.

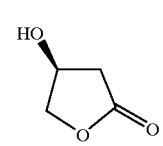

(1)

23 Claims, 3 Drawing Sheets

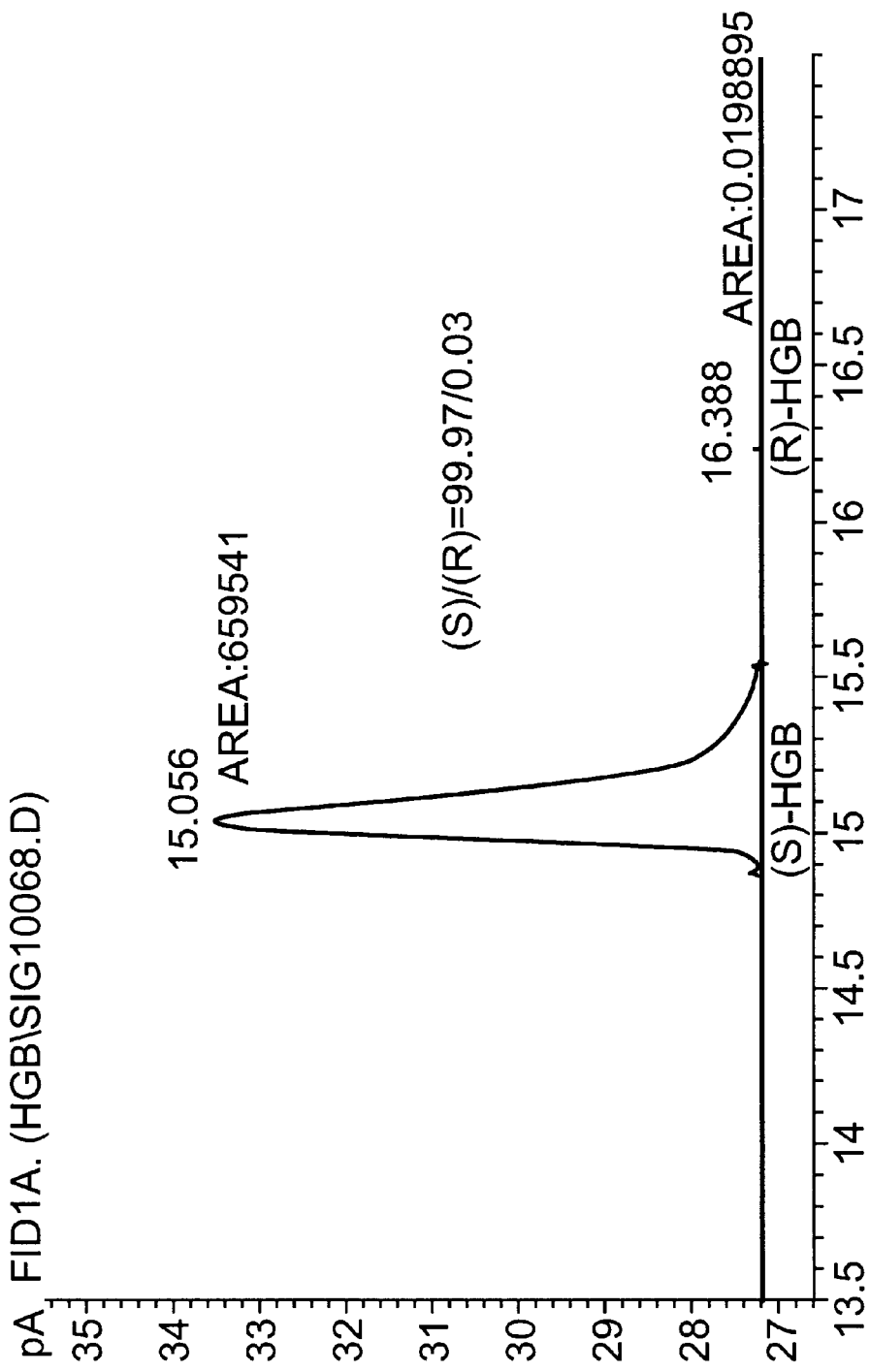

PROCESS FOR PREPARING OPTICALLY PURE (S)-3-HYDROXY-γ-BUTYROLACTONE

BACKGROUND OF THE INVENTION

1. Field of the Invention

The present invention relates to a process for preparing optically pure (S)-3-hydroxy-γ-butyrolactone expressed by the following Formula 1 and more particularly, to a process that enables preparing optically pure (S)-3-hydroxy-γ-butyrolactone economically in large quantities, by:

(a) Preparing α-(1,4) linked oligosaccharide having adequate sugar distribution by reacting amylopectin which is easily available from natural product with enzyme under a specific condition; and (b) Performing oxidatioin, esterification and cyclization sequentially under a specific condition.

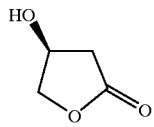

(1)

2. Description of the Related Arts (S)-3,4-Dihydroxybutyric acid derivatives and (S)-3-hydroxy-γ-butyrolactone are used as synthetic intermediates for preparing various chiral compounds. For example, it is well known that they act as key intermediates for preparing neuromeidator (R)-GABOB [*Tetrahedron*, 46, 4277(1990)], treatment for hyperlipemia (Atorvastatin; HMG-CoA reductase inhibitor) [*Tetrahedron Lett.*, 33, 2279(1992)], (S)-oxiracetam which is improvement agent in brain metabolism [International patent publication WO93/06,826], L-carnitine which is health supplement agent [International patent publication WO99/05,092], (S)-3-hydroxytetrahydrofuran [*J. Am. Chem. Soc.*, 117, 1181(1995); International patent publication WO94/05,639] which is an essential intermediate of AIDS drug (Agenerase; HIV protease inhibitor), (S)-monobetalactam [Japanese patent publication 64-13,069(1989)], ester of (S)-3-hydroxy-4-bromobutyric acid [Japanese patent publication 4-149,151(1992); Japanese patent publication 6-172,256(1994)], potentiating intermediate of satiety agent [*Bull. Chem. Soc. Jpn.*, 61, 2025(1988)] and neuroleptic drug [U.S. Pat. No. 4,138,484] and useful intermediates in synthetic efforts towards natural products [*J. Org. Chem.*, 50, 1144 (1985); Can. *J. Chem.*, 65, 195 (1987), *Tetrahedron Lett.*, 507 (1992)]. Optical purity is the most important factor in preparing these chiral compounds.

The conventional technologies for preparing (S)-3,4-dihydroxybutyric acid derivatives and (S)-3-hydroxy-γ-butyrolactone, which are useful for preparing the said chiral compounds, are explained in detail hereunder.

Methods of preparing (S)-3-hydroxybutyric acid derivatives from the enzymatic or catalytic reduction of β-ketoester were known [*J. Am. Chem. Soc.*, 105, 5925~5926(1983); *Teterahedron Lett.*, 31, 267~270(1990); European patent publication 452,143A2]. These methods have difficulty in that the prochiral center should be reduced to one-side to generate chiral center and expensive metal catalyst should be used.

A technology preparing ester of (S)-3,4-dihydroxybutyric acid and (S)-3-hydroxy-γ-butyrolactone by selective reduction of (L)-malic acid ester was known [*Chem. Lett.*, 1389~1392(1984); U.S. Pat. No. 5,808,107]. This technology has disadvantage in that reduction should be performed selectively to only one of the two ester functional groups.

Many methods of preparing (S)-3,4-dihydroxybutyric acid derivatives and (S)-3-hydroxy-γ-butyrolactone from carbohydrate have been reported.

A technology preparing isosaccharinic acid (B) or (S)-3,4-dihydroxybutyric acid (C) is reported [*J. Chem. Soc.*, 1924~1931(1960)] by alkaline degradation of carbohydrate containing glucose substituent in the 4-position, such as 4-O-methyl-(D)-glucose, maltose, amylose and cellulose, elimination of C-4 substituent as leaving group, forming dicarbonyl compound (A; 4-deoxy-2,3-hexodiulose), and reacting the formed dicarbonyl compound with base as shown in Scheme 1. However, the yield of (S)-3,4-dihydroxybutyric acid is low.

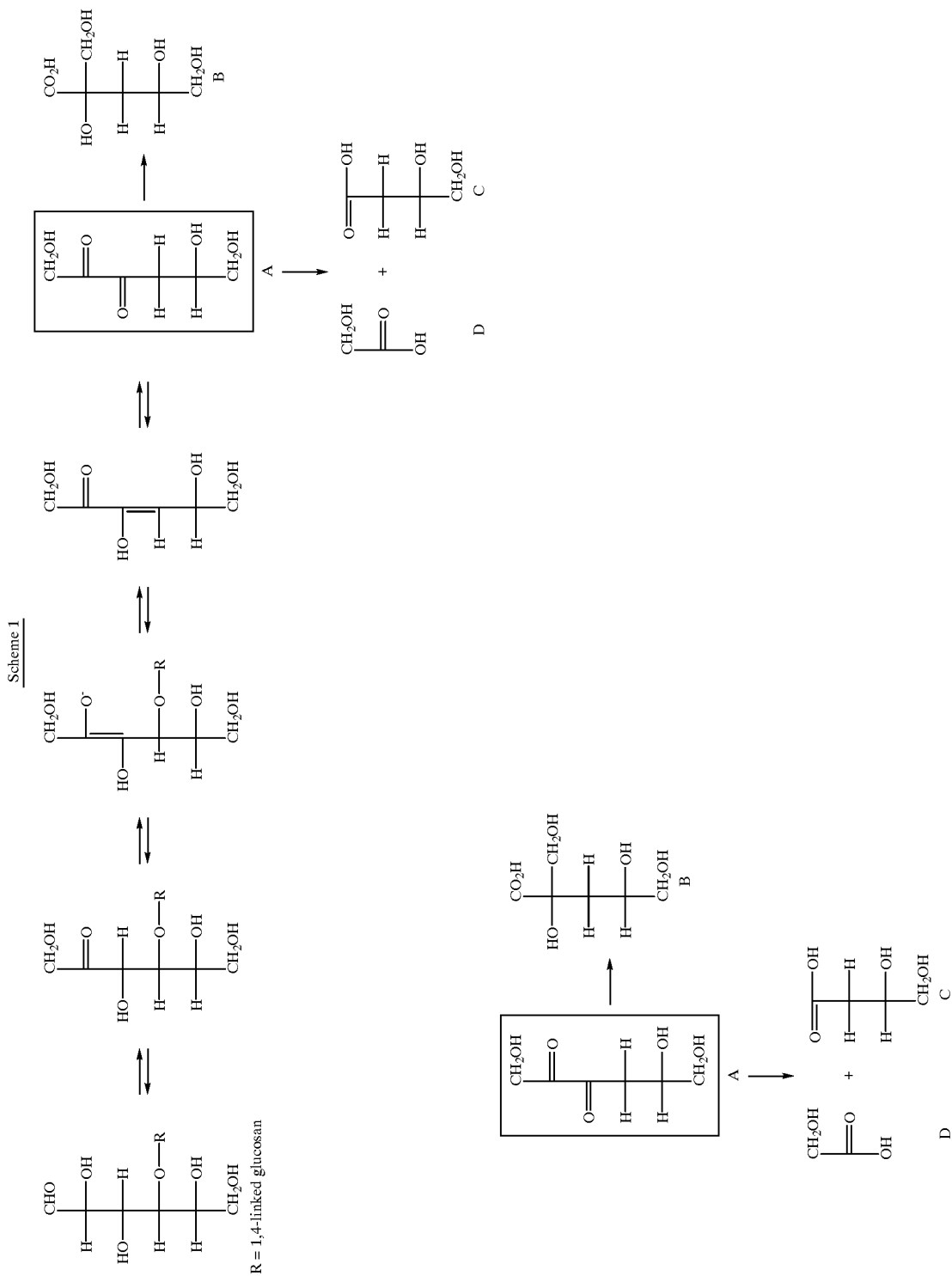

Also, it has been reported that (S)-3,4-dihydroxybutyric acid (C) and glycolic acid (D) were obtained as major products by forming dicarbonyl compound (A) from alkaline degradation of carbohydrate containing glucose substituent in the 4-position, and separating the formed dicarbonyl compound (A) and reacting it with hydrogen peroxide [J. Chem. Soc., 1932~1938(1960)]. This method has a serious problem that the product exists as small amount of isomers due to tautomerization and a mixture of cyclic compounds and hydrates derived from dicarbonyl compound (A). So, the dicarbonyl compound (A) cannot be separated in good yields from the reaction mixture. Another problem is that the prepared (S)-3,4-dihydroxybutyric acid is degraded to formic acid and glycolic acid due to the overoxidation.

A similar technology for preparing (S)-3,4-dihydroxybutyric acid from carbohydrate either using base only or using oxygen in base was known. It proposed that the dicarbonyl compound (A) was a synthetic intermediate for (S)-3,4-dihydroxybutyric acid as shown in the Scheme 1. But the yield was reported to be as low as about 30% [J. Res. Natl. Bur. Stand., 32, 45(1944); J Am. Chem. Soc., 2245~2247(1953); J. Am. Chem. Soc., 1431~1435(1955); Carbohyd. Res., 11, 17~25(1969); J. Chromatography, 549, 113~125(1991)]. In these methods, (S)-3,4-dihydroxybutyric acid is produced with various kinds of mixtures including glycolic acid (D), isosaccharinic acid (B), formic acid, ketone, diketone and glyceric acid. Since the yield of (S)-3,4-dihydroxybutyric acid is very low, these methods are also considered as not suitable for industrial use.

A method for preparing (S)-3,4-dihydroxybutyric acid from disaccharide (lactose) using base and oxidant has been reported [International patent publication WO98/04543]. In this work, (S)-3,4-dihydroxybutyric acid was cyclized to (S)-3-hydroxy-γ-butyrolactone under the reaction condition and purified by protection of the two hydroxy groups to acetonide ester compound, methyl (S)-3,4-O-isopropylidene-3,4-dihydroxybutanoate, which was recycled to (S)-3-hydroxy-γ-butyrolactone under acidic media.

Preparing methods of (S)-3,4-dihydroxybutyric acid including the process of alkaline oxidation of carbohydrate containing glucose substituent in the 4-position have been known [U.S. Pat. No. 5,292,939, 5,319,110 & 5,374,773(1994)]. In these methods, dicarbonyl compound (A) intermediate is formed at first, oxidized to (S)-3,4-dihydroxybutyric acid (C) and glycolic acid (D). However, optical purity, the most important physical property of chiral compounds, is not mentioned at all. Also, purification of target compound is very difficult, considering the reaction mechanism. In the case of disaccharides such as maltose or lactose, only one sugar unit in the disaccharide forms (S)-3,4-dihydroxybutyric acid and the other sugar unit functions as leaving group, so that the target product and leaving group coexist as 1:1 mixture. Accordingly, it is very difficult to separate and purify (S)-3,4-dihydroxybutyric acid or (S)-3-hydroxy-γ-butyrolactone from the reaction mixture. The maximum mass conversion obtainable is 28.3 wt %. In other words, 28.3 g of (S)-3-hydroxy-γ-butyrolactone can be obtained from 100 g of disaccharide. For polysaccharides, such as maltodextrin, starch and cellulose, mentioned in the above patents, the (1,4) and/or (1,6) glucose units are linked complexly like nets. The problem is that the step-by-step oxidation proceeding from the reducing end units comprising (1,4) linkage terminates at (1,6) linkage unit. Therefore, no more target product is formed. Also, the polysaccharides are degraded by overoxidation of reducing end units to complex acid mixtures containing formic acid, oxalic acid, glycolic acid and erythronic acid [J. Am. Chem. Soc., 81, 3136(1959); Starch 41 Nr. 8, S. 303~309(1989); Synthesis, 597~613(1997)].

There was an attempt to improve the yield of (S)-3,4-dihydroxybutyric acid or (S)-3-hydroxy-γ-butyrolactone for polysaccharide by degradation of higher-molecular sugars to relatively lower-molecular sugars through acid or base hydrolysis. Though the reactivity by this method is increased to a degree, (1,4) linkage and (1,6) linkage are not hydrolyzed selectively to afford random distribution. Accordingly, there is a fundamental problem in preparing (S)-3,4-dihydroxybutyric acid derivatives in high yield [Encyclopedia of Chemical Technology, 3rd ed. 492~507].

Regarding the preparation of (S)-3-hydroxy-γ-butyrolactone using (1,4) linked polysaccharide, the step-by-step oxidation proceeds continuously from the reducing end units to non-reducing end units to afford (S)-3,4-dihydroxybutyric acid until the last chain unit (leaving group) remains. Namely, if (1,4)-linked polysaccharide is used as a source material for preparing (S)-3-hydroxy-γ-butyrolactone, the maximum mass conversion obtainable is 63 wt %, about two times more compared with the method using disaccharide. In other words, 63 g of (S)-3-hydroxy-γ-butyrolactone can be obtained from 100 g of (1,4)-linked polysaccharide. Also, since the small amount of leaving group is produced in the reaction mixture compared with disaccharide, the target product is easily purified. Therefore, the use of (1,4)-linked polysaccharide promises the enhanced productivity.

However, regarding conventional polysaccharides, the target product and by-products (acids such as formic acid, oxalic acid, glycolic acid and erythronic acid) are formed competitively in the step-by-step oxidation due to the compact structure having random (1,4) linkage and (1,6) linkage. Thus, selective degradation technique of polysaccharide to a suitable sugar distribution range having (1,4) linkage is required.

On the other hand, there have been many reports of transforming higher-molecular sugars to lower-molecular sugars using biological enzymatic treatment process for industrial use.

The reported technologies include preparing glucose, maltose and ethanol through enzymatic treatment of starch [U.S. Pat. No. 3,791,865(1974); U.S. Pat. No. 3,922,200(1975); U.S. Pat. No. 4,855,232(1989): Japanese patent publication 4-158,795(1992); Methods Carbohydr. Chem., 10, 231~239(1994); Methods Carbohydr. Chem., 10, 245~248(1994)], and preparing maltodextrin with adequate dextrose equivalent (DE) [U.S. Pat. No. 3,986,890(1976); U.S. Pat. No. 4,447,532(1984); U.S. Pat. No. 4,612,284(1986); U.S. Pat. No. 5,506,353(1996)]. In these references, through the degradation or transformation of high molecular polysaccharides, they are converted to adequate materials for medicines, food additives and diagnostic reagents.

But, the method for preparing (1,4)-linked oligosaccharides suitable for the mass production of (S)-3-hydroxy-γ-butyrolactone by biological treatment of higher molecular polysaccharides with enzymes is not known at present.

SUMMARY OF THE INVENTION

The inventors of the present invention made intensive efforts to develop a method for preparing optically pure (S)-3-hydroxy-γ-butyrolactone from commercially available amylopectin with ease. As a results, a process which enables preparing optically pure (S)-3-hydroxy-γ-butyrolactone economically in large quantities is found by preparing oligosaccaride with structural specificity which can minimize formation of by-products from amylopectin by enzymatic reaction. Furthermore, oxidation reaction can be performed continuously in the same reactor without additional separation and purification of the prepared oligosaccharide.

Accordingly, an object of this invention is to provide a method for preparing optically pure (S)-3-hydroxy-γ-butyrolactone in high yield without additional purification of intermediates.

BRIEF DESCRIPTION OF THE DRAWINGS

FIG. 1c represents the optical purity analysis results by gas chromatography (GC) of 3-hydroxy-γ-butyrolactone prepared from oligosaccharide of the present invention.

DETAILED DESCRIPTION OF THE INVENTION

Figure 1A:
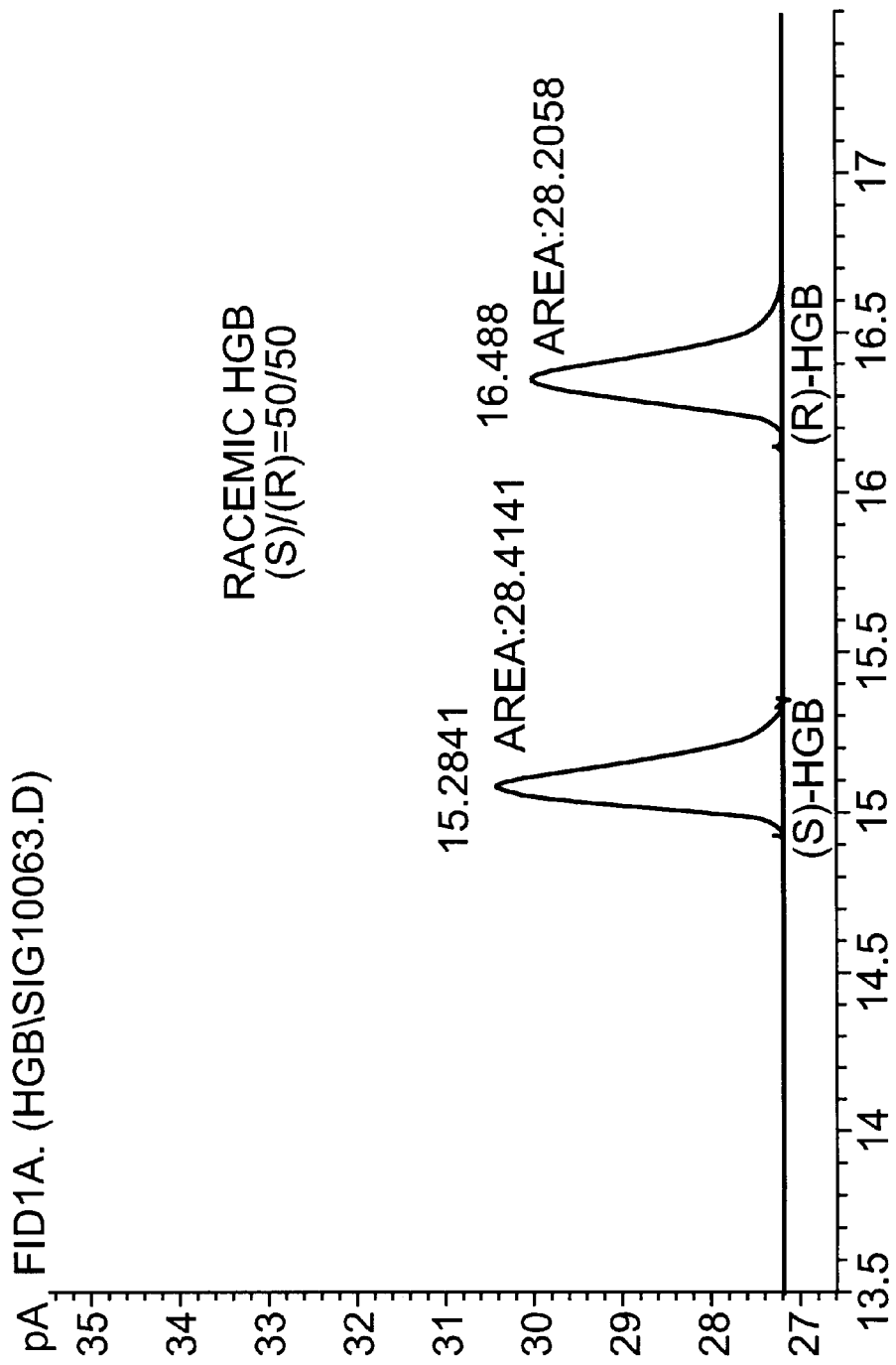
FIG. 1a represents the optical purity analysis results by gas chromatography (GC) of racemic 3-hydroxy-γ-butyrolactone.

The present invention is characterized by comprising the following steps:
(a) Enzymatic reaction of amylopectin to α-(1,4)-linked oligosaccharide expressed by the Formula 2;
(b) Oxidation of the oligosaccharide with oxidant in base, and subsequent esterification with alcohol in the presence of an acid catalyst to afford ester of (S)-3,4-dihydroxybutyric acid expressed by the Formula 3; and
(c) Cyclization of the prepared ester of (S)-3,4-dihydroxybutyric acid in the presence of an acid catalyst without additional separation and purification process to afford (S)-3-hydroxy-γ-butyrolactone expressed by the Formula 1.

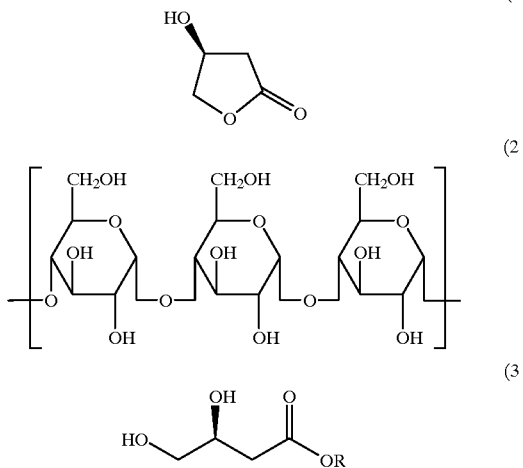

wherein, R represents linear or branched alkyl group with 1~5 carbons.

The detailed description of the present invention is given hereunder.

The fundamental inventive concept of the present invention is selective degradation of α-(1,4) linkage and α-(1,6) linkage within amylopectin using specific enzymes, i.e., transforming amylopectin to α-(1,4) linked oligosaccharide with the optimal sugar distribution for preparing the target compound. And subsequently oxidation, esterification and cyclization are performed to prepare (S)-3-hydroxy-γ-butyrolactone.

Namely, focusing on the specificity of enzymes, amylopectin is degraded sequentially with specific enzymes to α-(1,4) linked oligosaccharide, and optically pure (S)-3-hydroxy-γ-butyrolactone is prepared from the transformed oligosaccharide in high yield.

Amylopectin, source material of the present invention, is commercially easily available. Especially, since amylopectin is highly soluble in water or in buffer solution of pH 4.0~8.0, used as reaction solvent for enzymatic reaction of the present invention, the relative reactivity to enzyme is greatly increased compared with other polysaccharides such as starch and cellulose. Thus, the same is very effective material for preparing of oligosaccharide having suitable sugar distribution for the preparation of (S)-3-hydroxy-γ-butyrolactone.

When using pullulanase as an enzyme for selective degradation of α-(1,6) linkage in amylopectin, it causes the solubility problem of amylopectin and reduced enzyme activity. So, rather than using pullulanase only, α-amylase was used to improve reactivity in degrading amylopectin to a suitable sugar distribution, and then pullulanase was used. However, in this case, activity of the remaining α-amylase persists and thus amylopectin is degraded excessively, so that the desired oligosaccharide is not formed. Accordingly, a technology of inactivating the remaining α-amylase before the pullulanase reaction was introduced.

Preferably, the preparation process of this invention is as follows: 1) a step preparing oligosaccharide with characteristic α-(1,4) linkage expressed in Formula 2 by selective degradation of amylopectin using biological treatment of specific enzymes, 2) a step preparing ester of (S)-3,4-dihydroxybutyric acid through oxidation, and 3) a step preparing optically pure (S)-3-hydroxy-γ-butyrolactone in high yield through cyclization of the prepared ester compound. Especially, the preparation process of this invention is characterized by preparing (S)-3-hydroxy-γ-butyrolactone in the same reactor without additional purification of the intermediates (oligosaccharide and ester of (S)-3,4-dihydroxybutyric acid).

The enzymatic reaction of the present invention uses α-amylase and pullulanase sequentially. α-Amylase degrades α-(1,4) linkage and pullulanase degrades α-(1,6) linkage selectively.

The superiority of the present invention lies in that optically pure (S)-3-hydroxy-γ-butyrolactone is prepared in high yield under a mild reaction condition by using enzymes selectively degrading α-(1,4) linkage or α-(1,6) linkage, while the chemical hydrolysis method has no selectivity.

The enzymatic reaction of the present invention is performed in water or buffer solution of pH 4.0~8.0 at 40~120° C. α-Amylase is used in the range of 0.001~10 wt % of amylopectin, and enzymatic reaction of α-amylase is performed for 30 min~4 hr, and then remaining α-amylase is inactivated. Inactivation is performed under acidic (pH 2.0~4.5) and high temperature (60~150° C.) conditions and maintained for 10 min~4 hr. In the enzymatic reaction of pullulanase, pullulanase is used in the range of 0.001~10 wt % of amylopectin, and most of the oligosaccharides distribute within 3~50 glucose units by 10~40 hr of the pullulanase enzymatic treatment. Reducing end units and molecular weight distribution of the prepared oligosaccharide are analyzed from reducing end units and dextrose equivalent analysis by an optical analyzer, HPLC analysis, and gel permeation chromatography (GPC) analysis.

The oligosaccharide is obtained from the selective enzymatic reaction and has distribution mostly between 3~50 glucose units, and preferably 5~50 glucose units. Since most of the glucose units are linked with α-(1,4) linkage, (S)-3-hydroxy-γ-butyrolactone can be obtained in high yield through continuous sequential reactions with minimizing the by-products (e.g., acid mixtures of formic acid, oxalic acid, glycolic acid and erythronic acid). Furthermore, the obtained (S)-3-hydroxy-γ-butyrolactone was identified to be optically very pure (>99.9%ee).

Oxidation of oligosaccharide is performed by adding base and oxidant dropwise for 6~36 hr under the condition of 30~65° C. Hydrogen peroxide, alkali metal peroxides, akaline earth metal peroxides and alkyl hydroperoxides are used for the oxidants, and hydrogen peroxide is the most preferable. Preferably, the oxidant is t-butylhydroperoxide. The oxidant is used in the range of 1~3 equivalents per molar glucose unit of amylopectin. The base is selected from the group consisting of alkali metal hydroxide or alkaline earth metal hydroxide, and sodium hydroxide or potassium hydroxide is preferable. The base is used in the range of 2~4 equivalents per molar glucose unit of amylopectin.

The preparation yields of (S)-3-hydroxy-γ-butyrolactone depending on the source material are compared as follows [Refer to Experimental example 1.]. If maltose (disaccharide) or lactose (disaccharide) obtained from cheese byproduct is used as source material, the theoretical mass conversion yield of (S)-3-hydroxy-γ-butyrolactone is not more than 28.3 wt % of the source material weight used. On the other hand, if amylose (α-(1,4) linked polysaccharide) with more than 50 glucose units is used, the theoretical mass conversion yield of (S)-3-hydroxy-γ-butyrolactone is equal to that of amylopectin. But, the double helix structure due to very strong intramolecular hydrogen bond limits the step-by-step oxidation, so the yield becomes very low. However, by using oligosaccharide of the present invention as source material, the yield of (S)-3-hydroxy-γ-butyrolactone is very high as 57.2 wt % of the source material weight used.

In order to synthesize (S)-3-hydroxy-γ-butyrolactone from the prepared (S)-3,4-dihydroxybutyric acid, esterification and cyclization are performed sequentially.

Esterification of the present invention is performed in the presence of acid catalyst using alcohol as both solvent and reagent in the temperature range of 30~80° C. Inorganic acids such as hydrochloric acid, sulfuric acid, phosphoric acid and nitric acid, or organic acids such as fluoroalkylsulfonic acid, aralkylsulfonic acid, hydrate of aralkylsulfonic acid and trifluoroacetic acid are used as acid catalyst. Linear or branched alcohol with 1~5 carbon atoms is used for the alcohol.

Ester of (S)-3,4-dihydroxybutyric acid expressed in the Formula 3 produced from the esterification is cyclized at the temperature range of 30~80° C. for 2~5 hr in to afford (S)-3-hydroxy-γ-butyrolactone. Inorganic acid such as hydrochloric acid, sulfuric acid, phosphoric acid and nitric acid or organic acid such as fluoroalkylsulfonic acid, aralkylsulfonic acid, hydrate of aralkylsulfonic acid and trifluoro acetic acid is used for the acid catalyst.

According to the conventional method of preparing (S)-3-hydroxy-γ-butyrolactone from (S)-3,4-dihydroxybutyric acid derivatives disclosed in U.S. Pat. No. 5,319,110, various side products including glucose leaving groups and glycolic acid are mixed substantially with the target product. Also, since (S)-3-hydroxy-γ-butyrolactone is highly soluble in water, it is very difficult to separate and purify from the aqueous reaction solution. In WO98/04543, (S)-3,4-dihydroxybutyric acid was cyclized to (S)-3-hydroxy-γ-butyrolactone under the reaction condition and purified by protection of the two hydroxy groups to acetonide ester compound, methyl (S)-3,4-O-isopropylidene-3,4-dihydroxybutanoate, which was recyclized to (S)-3-hydroxy-γ-butyrolactione under acidic media. In this method, additional procedures are required after obtaining the target product because methyl (S)-3,4-O-isopropylidene-3,4-dihydroxybutanoate with the dihydroxy group protected should be separated and cyclized by adding acid to obtain (S)-3-hydroxy-γ-butyrolactone.

On the other hand, in the preparing method of the present invention, after (S)-3,4-dihydroxybutyric acid is obtained, water used for the reaction solvent is removed by distillation and then, acid catalyst and alcohol solvent are added to obtain (S)-3,4-diydroxybutanoate ester. Impurities such as salts are removed by filtration and the same is heated under reduced pressure in the presence of acid catalyst to afford (S)-3-hydroxy-γ-butyrolactone by cyclization in high yield. Therefore, the present invention provides an advantage of simple preparing routes and enables the sequential reactions to take place in the same reactor and thereby produces (S)-3-hydroxy-γ-butyrolactone in large quantities.

As explained above, the present invention is excellent in that the low reactivity of amylopectin to oxidation is overcome by transforming amylopectin to oligosaccharide with the application of specific enzymes. Furthermore, byproduct formation is minimized and optically pure (S)-3-hydroxy-γ-butyrolactone can be prepared in high yield with very simple purification process.

The following examples are intended to be illustrative of the present invention and should not be construed as limiting the scope of this invention defined by the appended claims.

EXAMPLE 1

Preparation of methyl (S)-3,4-dihydroxybutanoate

10 L of water and 5 kg of dried amylopectin were put into a 50 L reactor. After heating the reactor to 55° C., 12 g of α-amylase (BAN; EC 3.2.1.1 from *Bacillus licheniformis*, Novo Nordisk) was added. After heating this reaction solution to 75° C., the same was stirred for 2 hr at the same temperature. 5 mL of 0.1N HCl solution was added to adjust the pH of the reaction solution to 3.0~3.5, and then the same was stirred for 1 hr at 90° C. to inactivate the remaining α-amylase. After slowly cooling the reaction mixture to 30° C., 3.7 L of 4M acetic acid buffer solution (pH 5) and 1.3 L of water were added to adjust the pH to 5. The reaction solution was heated to 60° C., and then 62.5 g of pullulanase (Promozyme; EC 3.2.1.4 from *Bacillus acidopullulyticus*, Novo Nordisk) was added and the solution was stirred for 22 hr at the same temperature. 0.54 kg of 40% NaOH solution was added to the reaction solution to neutralize acetic acid and the temperature was raised to 60° C. 40% NaOH (8.64 kg) solution and 30% $H_2O_2$ (5.25 kg) solution were added dropwise for 24 hr to the reaction solution and the same was stirred for 1 hr at the same temperature. The prepared sodium salt of (S)-3,4-dihydroxybutyric acid was identified using NMR analysis.

$^1$H-NMR ($D_2O$, ppm) δ 2.27 (dd, 1H), 2.39 (dd, 1H), 3.41 (dd, 1H), 3.51 (dd, 1H), 3.8~3.9 (m, 1H)

The reaction solution was concentrated, and 10 L of methanol was added. Sulfuric acid were added to adjust the pH to 4~5, and then the same was stirred for 3 hr at 50° C. Sodium carbonate was added to neutralize the solution, and the same was filtered to remove the by-product, and then methanol was concentrated to obtain methyl (S)-3,4-dihydroxybutanoate. The formation of methyl (S)-3,4- dihydroxybutanoate (conversion ratio: 92%) was identified through NMR analysis with the comparison of internal standard.

$^1$H-NMR (CDCl$_3$, ppm) δ 2.5 (dd, 2H), 3.5 (dd, 1H), 3.6 (dd, 1H), 3.7 (s, 3H), 4.1 (m, 1H)

EXAMPLE 2

Preparation of (S)-3-hydroxy-γ-butyrolactone

10 L of water and 5 kg of dried amylopectin were put into a 50 L reactor. After heating the reactor to 55° C., 12g of α-amylase (Teramyl; EC 3.2.1.1 from *Bacillus amyloliquefaciens*, Novo Nordisk) was added. After heating this reaction solution to 85° C., the same was stirred for 2 hr at the same temperature. 5mL of 0.1N HCl solution was added to adjust the pH of the reaction solution to 3.0~3.5, and then the same was stirred for 1 hr at 90° C. to inactivate the remaining α-amylase. After slowly cooling the reaction to 30° C., 3.7 L of 4M acetic acid buffer solution (pH 5) and 1.3 L of water were added to adjust the pH to 5. The reaction solution was heated to 60° C., and then 62.5 g of pullulanase (Promozyme; EC 3.2.1.4 from *Bacillus acidopullulyticus*, Novo Nordisk) was added and the solution was stirred for 22 hr at the same temperature. 0.54 kg of 40% NaOH solution was added to the reaction solution to neutralize acetic acid and the temperature was raised to 60° C. 40% NaOH (8.64 kg) solution and 30% H$_2$O$_2$ (5.25 kg) solution were added dropwise for 24 hr to the reaction solution and the same was stirred for 1 hr at the same temperature. The prepared sodium salt of (S)-3,4-dihydroxybutyric acid was identified using NMR analysis.

$^1$H-NMR (D$_2$O, ppm) δ 2.27 (dd, 1H), 2.39 (dd, 1H), 3.41 (dd, 1H), 3.51 (dd, 1H), 3.8~3.9 (m, 1H)

The reaction solution was concentrated, and 10 L of methanol was added. In this solution, methanesulfonic acid was added to adjust the pH to 4~5, and then the same was stirred for 3 hr at 50° C. After cooling, sodium carbonate was added to neutralize the solution, and the same was filtered to remove the by-product, and then methanol was concentrated to obtain methyl (S)-3,4-dihydroxybutanoate. Formation of methyl (S)-3,4-dihydroxybutanoate (conversion ratio: 93%) was identified using NMR analysis comparing with the internal standard.

$^1$H-NMR (CDCl$_3$, ppm) δ 2.5 (dd, 2H), 3.5 (dd, 1H), 3.6 (dd, 1H), 3.7 (s, 3H), 4.1 (m, 1H)

The prepared methyl (S)-3,4-dihydroxybutanoate was cyclized at 65° C. under reduced pressure by adding 0.5 wt % of concentrated HCl without any separation. The resultant solution was dissolved with ethyl acetate and the same was neutralized with sodium carbonate. After filtering and concentrating the same, (S)-3-hydroxy-γ-butyrolactone (2.86 kg, 57.2 wt % of the amylopectin weight used) was obtained.

$^1$H-NMR (CDCl$_3$, ppm) δ 2.28 (dd, 1H), 2.74 (dd, 1H), 4.13 (dd, 1H), 4.32 (dd, 1H), 4.4~4.5 (m, 1H)

EXAMPLE 3

Preparation of (S)-3-hydroxy-γ-butyrolactone

As in the Example 2, however using 1 wt % of methanesulfonic acid rather than concentrated HCl in the cyclization of the prepared methy (S)-3,4-dihydroxybutanoate, the same was cyclized at 65° C. under reduced pressure. The resultant solution was dissolved with ethyl acetate and the same was neutralized with sodium carbonate. After filtrating and concentrating the same, (S)-3-hydroxy-y-butyrolactone (2.85 kg, 57 wt % of the amylopectin weight used) was obtained.

1H-NMR (CDCl$_3$, ppm) δ 2.28 (dd, 1H), 2.74 (dd, 1H), 4.13 (dd, 1H), 4.32 (dd, 1H), 4.4~4.5 (m, 1H)

EXAMPLE 4

Preparation of methyl (S)-3,4-dihydroxybutanoate

As in the Example 1, however using t-butylhydroperoxide (4.16 kg) rather than H$_2$O$_2$ for the oxidant, methyl (S)-3,4-dihydroxybutanoate was obtained. The formation of methyl (S)-3,4-dihydroxybutanoate (conversion ratio: 91%) was identified using NMR analysis from the comparison with internal standard.

1H-NMR (CDCl$_3$, ppm) δ 2.5 (dd, 2H), 3.5 (dd, 1H), 3.6 (dd, 1H), 3.7 (s, 3H), 4.1 (m, 1H)

Comparative Example 1

Preparation of (S)-3-hydroxy-γ-butyrolactone from starch

20 L of water and 5 kg of dried starch were put into a 50 L reactor, and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was esterified and cyclized as in Example 2 to obtain (S)-3-hydroxy-γ-butyrolactone (1.1 kg, 22.0 wt % of starch weight used).

Comparative Example 2

Preparation of (S)-3-hydroxy-γ-butyrolactone from starch

10 L of 0.5N HCl solution and 5 kg of dried starch were put into a 50 L reactor, and the starch was hydrolyzed for 20 min at 100° C. After cooling the solution to 20° C., the same was neutralized with 100 mL of 40% NaOH solution and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was esterified and cyclized as in Example 2 to obtain (S)-3-hydroxy-γ-butyrolactone (1.22 kg, 24.4 wt % of starch weight used).

Comparative Example 3

Preparation of (S)-3-hydroxy-γ-butyrolactone from amylose

20 L of water and 5 kg of dried amylose were put into a 50 L reactor, and the temperature was raised to 70° C. 40% NaOH (8.64 kg) solution and 30% H$_2$O$_2$ (5.25 kg) solution were added dropwise for 48 hr to the reaction solution and the same was stirred for 1 hr at the same temperature. The same was esterified and cyclized as in the Example 2 to obtain (S)-3-hydroxy-γ-butyrolactone (1.35 kg, 27.0 wt % of amylose weight used).

Experimental Example 1

Comparison of (S)-3-hydroxy-γ-butyrolactone yield depending on the source material For the reaction solutions containing each of the carbohydrates shown in Table 1, oxidation, esterification and cyclization were performed as in the Example 2 to obtain (S)-3-hydroxy-γ-butyrolactone. The yields of (S)-3-hydroxy-γ-butyrolactone are shown in Table 1.

TABLE 1

| Source material (5 kg) | Product (wt % compared with source material weight) |
| --- | --- |
| Oligosaccharide of the present invention (Example 2) | 2.86 kg (57.2 wt %) |
| Polysaccharide    Amylopectin | 1.01 kg (20.2 wt %) |
| Amylose | 1.35 kg (27.0 wt %) |
| Disaccharide (maltose)[a] | 1.19 kg (23.7 wt %) |

[a]Examples 1 & 2 of U.S. Pat. Nos. 5,292,939, 5,319,110 & 5,374,773

Table 1 shows that for disaccharide the relative mass conversion yield is low as 23.7 wt %. On the other hand, if amylopectin is transformed to oligosaccharide with specific enzyme treatment, the relative mass conversion yield is enhanced to 57.2 wt % almost two times compared with disaccharide. If amylopectin is not treated with enzymes, the relative mass conversion yield is relatively low as 20.2 wt %.

Experimental Example 2

Optical purity analysis of (S)-3-hydroxy-γ-butyrolactone (S)-3-Acetoxy-γ-butyrolactone was synthesized by the following method in order to analyze optical purity of (S)-3-hydroxy-γ-butyrolactone prepared from the present invention and the conventional preparing method.

102 mg (1 mmol) of (S)-3-hydroxy-γ-butyrolactone prepared from each method was dissolved in 3 mL of methylene chloride, and 0.4 mL (5 mmol) of pyridine and 0.47 mL (5 mmol) of acetic anhydride were added to the same. After 3 hr, the reaction was quenched with 1N HCl. (S)-3-Acetoxy-γ-butyrolactone was extracted with the methylene chloride. After work up, the same was purified with silica gel column chromatography. The obtained (S)-3-acetoxy-γ-butyrolactone was dissolved in methylene chloride, and 0.5° C. was taken with syringe for GC analysis. The result is shown in the following Table 2 and FIGS. 1a–1c.

TABLE 2

| Source Material | Optical Purity |
| --- | --- |
| Disaccharide (maltose)[a] | 94% ee |
| Oligosaccharide of the present invention (Example 2) | 99.9% ee |

[a]Examples 1 & 2 of U.S. Pat. Nos. 5,292,939, 5,319,110 & 5,374,773

Figure 1B:
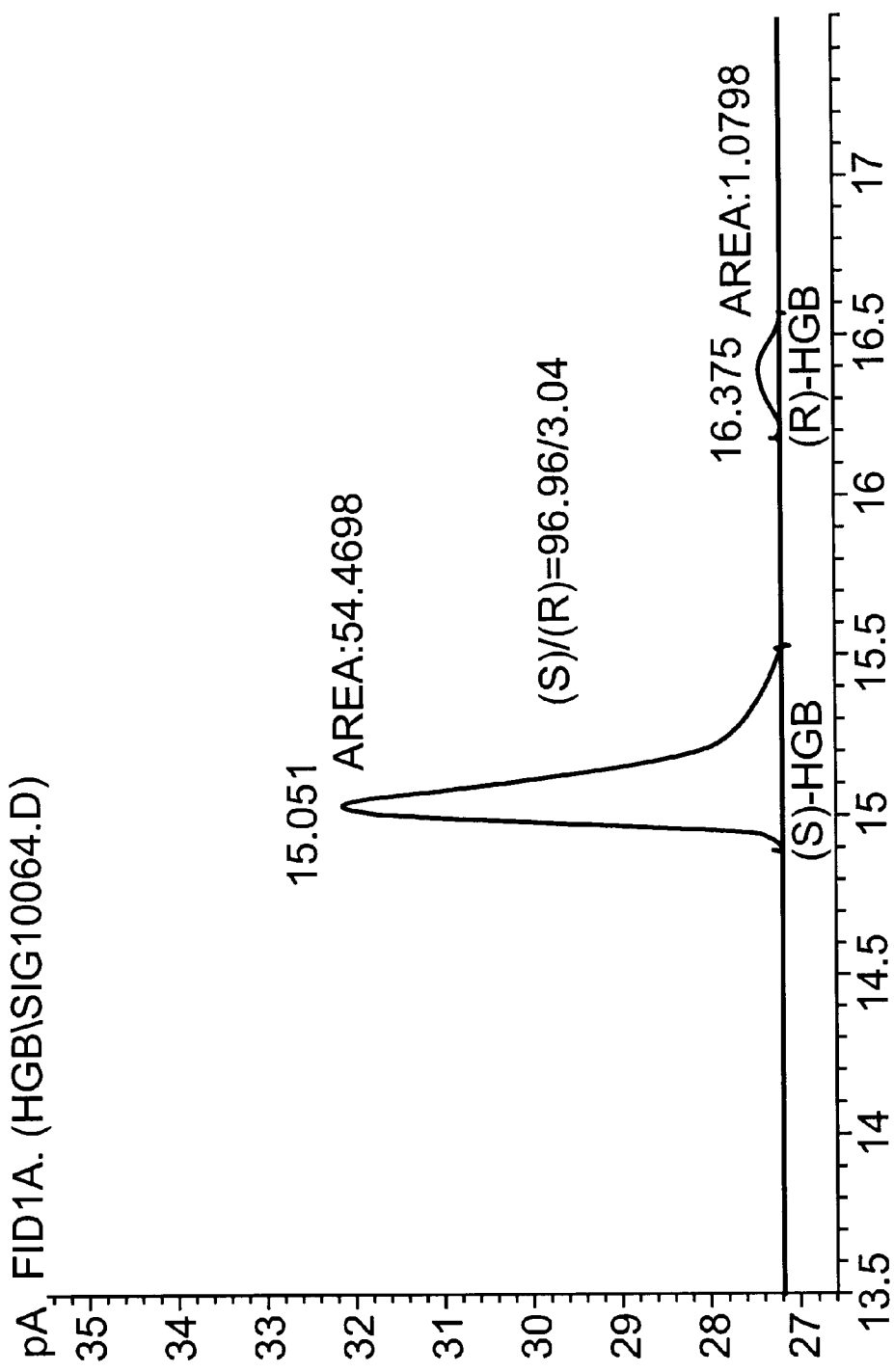
FIG. 1b represents the optical purity analysis results by gas chromatography (GC) of 3-hydroxy-γ-butyrolactone prepared from disaccharide of the conventional method.

To improve the medicinal efficiency and minimize the side effect, more than 99.5%ee of high optical purity is required for chiral compounds. Table 2 and FIGS. 1a–1c show that the optical purity of (S)-3-hydroxy-γ-butyrolactone prepared from the present invention is very high as 99.9%ee. So, the same is very useful for the intermediates of other chiral compounds. The results are illustrated in FIGS. 1a, 1b and 1c, respectively.

The preparing method of the present invention gives optically pure (S)-3-hydroxy-γ-butyrolactone, which is very useful for industrial uses because the by-product formation is minimized and the purification process is very simple. It comprises alkaline oxidation of α-(1,4) linked oligosaccharide from the enzymatic reaction of amylopectin in a specific condition followed by esterifying and cyclizing to afford the target product. The present invention has overcome the disadvantage of using expensive metal catalyst for selective asymmetric reduction, and enables easy preparation from inexpensive natural product having optically pure chiral center, thereby the industrial utility as chiral intermediates of various medicine can be maximized. Furthermore, the relative mass conversion yield is almost double compared with disaccharides.

What is claimed is:

1. A process for producing optically pure (S)-3-hydroxy-γ-butyrolactone expressed by the following Formula 1 from polysaccharide source, which comprises the following steps:

(a) Enzymatic reaction of amylopectin to α-(1,4) linked oligosaccharide expressed by the Formula 2;

(b) Oxidation of the oligosaccharide with oxidant in base, and subsequent esterification with alcohol in the presence of an acid catalyst to afford ester of (S)-3,4-dihydroxybutyric acid expressed by the Formula 3; and (c) Cyclization of the prepared ester of (S)-3,4-dihydroxybutyric acid in the presence of an acid catalyst without additional separation and purification process to form (S)-3-hydroxy-γ-butyrolactone expressed by the Formula 1,

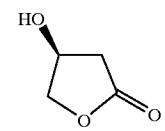

(1

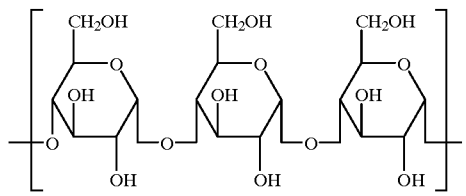

(2

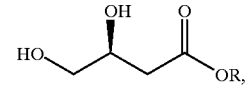

(3 wherein R represents linear or branched alkyl group with 1~5 carbon atoms.

2. The process according to claim 1, wherein the said enzymatic reaction is performed in water or in pH 4~8 buffer solution.

3. The process according to claim 1, wherein the said enzymatic reaction is performed by α-amylase enzymatic reaction followed by pullulanase enzymatic reaction.

4. The process according to claim 3, wherein the said α-amylase enzymatic reaction is performed under the condition of pH 4.0~8.0 and temperature of 40~120° C.

5. The process according to claim 3, wherein the said α-amylase is used in the range of 0.001~10 wt % of amylopectin.

6. The process according to claim 3, wherein the said pullulanase enzymatic reaction is performed under the condition of pH 4.0~8.0 and temperature of 40~120° C.

7. The process according to claim 3, wherein the said pullulanase is used in the range of 0.001~10 wt % of amylopectin.

8. The process according to claim 3, wherein the remaining α-amylase after the α-amylase enzymatic reaction is inactivated under the condition of pH 2.0~4.5 and temperature of 60~150° C., before the pullulanase enzymatic reaction is performed.

9. The process according to claim 1, wherein the said oxidation is performed in the range of 30~65° C.

10. The process according to claim 1, wherein the base used in the said oxidation is selected from the alkali metal hydroxide and the alkaline earth metal hydroxide.

11. The process according to claim 10, wherein the said base is sodium hydroxide.

12. The process according to claim 1 or claim 10, wherein the said base is used in the range of 2~4 equivalents per molar glucose unit of amylopectin.

13. The process according to claim 1, wherein the oxidant used in the said oxidation is selected from hydrogen peroxide, alkali metal peroxide, alkaline earth metal peroxide and alkyl hydroperoxide.

14. The process according to claim 13, wherein the said oxidant is hydrogen peroxide.

15. The process according to claim 13, wherein the said oxidant is t-butylhydroperoxide.

16. The process according to claim 1 or claim 13, wherein the said oxidant is used in the range of 1~3 equivalents per molar glucose unit of amylopectin.

17. The process according to claim 1, wherein the said oligosaccharide has the 3~50 glucose units.

18. The process according to claim 1, wherein the acid catalyst used in the said esterification is an inorganic acid selected from hydrochloric acid, sulfuric acid, phosphoric acid and nitric acid.

19. The process according to claim 1, wherein the acid catalyst used in the said esterification is an organic acid selected from fluoroalkylsulfonic acid, aralkylsulfonic acid, hydrate of aralkylsulfonic acid and trifluoroacetic acid.

20. The process according to claim 1, wherein the said esterification is performed in the range of 30~80° C.

21. The process according to claim 1, wherein the acid catalyst used in the said cyclization is an inorganic acid selected from hydrochloric acid, sulfuric acid, phosphoric acid and nitric acid.

22. The process according to claim 1, wherein the acid catalyst used in the said cyclization is an organic acid selected from fluoroalkylsulfonic acid, aralkylsulfonic acid, hydrate of aralkylsulfonic acid and trifluoroacetic acid.

23. The process according to claim 1, wherein the said cyclization is performed in the range of 30~80° C.

* * * * *